US010300306B2

(12) United States Patent
Mougenot (10) Patent No.: US 10,300,306 B2
(45) Date of Patent: May 28, 2019

(54) HIGH-INTENSITY FOCUSED ULTRASOUND IRRADIATION (71) Applicant: KONINKLIJKE PHILIPS N.V., Eindhoven (NL)

(72) Inventor: Charles Mougenot, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 593 days.

(21) Appl. No.: 14/768,056

(22) PCT Filed: Feb. 11, 2014

(86) PCT No.: PCT/IB2014/058890
§ 371 (c)(1),
(2) Date: Aug. 14, 2015

(87) PCT Pub. No.: WO2014/128592
PCT Pub. Date: Aug. 28, 2014

(65) Prior Publication Data
US 2015/0375016 A1 Dec. 31, 2015

Related U.S. Application Data (60) Provisional application No. 61/768,774, filed on Feb. 25, 2013.

(51) Int. Cl.
*A61B 5/00* (2006.01)
*A61N 7/02* (2006.01)
(Continued)

(52) U.S. Cl.
CPC ................ *A61N 7/02* (2013.01); *A61B 5/015* (2013.01); *A61B 5/055* (2013.01); *A61B 8/13* (2013.01);
(Continued)

(58) Field of Classification Search
CPC .......... A61N 7/02; A61B 5/015; A61B 5/055; A61B 8/13; A61B 34/10
See application file for complete search history.

(56) References Cited

U.S. PATENT DOCUMENTS 4,938,217 A * 7/1990 Lele .................... A61N 7/02
601/3
6,428,477 B1 8/2002 Mason
(Continued)

FOREIGN PATENT DOCUMENTS

DE 60209222 T2 12/2006
WO WO 0078232 A1 * 12/2000 ............... A61N 7/02
(Continued)

OTHER PUBLICATIONS

Arora, "Direct thermal dose control of constrained focused ultrasound treatments: phantom and in vivo evaluation", Phys Med Biol. 2005.*
(Continued)

*Primary Examiner* — Tse W Chen
*Assistant Examiner* — Joanne M Hoffman (57) ABSTRACT The present invention provides n ultrasonic treatment device (10) for heating a portion of a subject of interest, comprising a ultrasonic irradiation unit (12) for generating high-intensity focused ultrasonic irradiation, whereby a beam path of the ultrasonic irradiation is movable along a trajectory for depositing ultrasonic energy within a target zone (22) of the subject of interest, and a control unit (20) for controlling the ultrasonic irradiation unit (12) to move the beam path of the ultrasonic irradiation along the trajectory and to apply an ultrasonic dose to the target zone (22), wherein the control unit (20) is adapted to receive temperature information of the target zone (22) and to control the ultrasonic irradiation unit (12) based on the received temperature information, and the control unit (20) is adapted to control the ultrasonic
(Continued)

irradiation unit (12) based on the temperature of a current (26) and at least one previous direction (28) of the beam path of the ultrasonic irradiation along the trajectory. The invention further provides a corresponding method for ultrasonic treatment and an ultrasonic treatment system, comprising the above ultrasonic treatment device (10) and a diagnostic imaging device for providing temperature information of a target zone (22) of the subject of interest, wherein the control unit (20) of the ultrasonic treatment device (10) is adapted to receive the temperature information from the diagnostic imaging device. By looking at the temperature or a thermal dose distribution along a previous direction of the beam path of the ultrasonic irradiation along the trajectory where the heating has been completed, an improved control of the treatment is achieved. Even if this previous sonication was different to the one currently applied, it represents a good indicator of the tissue and ultrasound system behavior.

19 Claims, 3 Drawing Sheets

(51) Int. Cl.

| | | |
|---|---|---|
| *A61B 5/01* | (2006.01) | |
| *A61B 5/055* | (2006.01) | |
| *A61B 8/13* | (2006.01) | |
| *A61B 34/10* | (2016.01) | |
| *A61B 17/00* | (2006.01) | |
| *A61N 7/00* | (2006.01) | |

(52) U.S. Cl.
CPC .... *A61B 34/10* (2016.02); *A61B 2017/00084* (2013.01); *A61N 2007/0078* (2013.01); *A61N 2007/0082* (2013.01); *A61N 2007/0091* (2013.01); *A61N 2007/0095* (2013.01)

(56) References Cited

U.S. PATENT DOCUMENTS

| | | | | |
|---|---|---|---|---|
| 7,771,418 | B2* | 8/2010 | Chopra | A61B 5/055 606/27 |
| 8,016,757 | B2* | 9/2011 | Kaczkowski | A61B 5/015 374/117 |
| 2001/0031922 | A1* | 10/2001 | Weng | A61B 17/0057 600/439 |
| 2008/0114274 | A1* | 5/2008 | Moonen | A61N 7/02 601/3 |
| 2008/0167555 | A1* | 7/2008 | Qian | A61N 7/02 600/439 |
| 2008/0183077 | A1 | 7/2008 | Moreau-Gobard et al. | |
| 2009/0012514 | A1 | 1/2009 | Moonen | |
| 2009/0062724 | A1* | 3/2009 | Chen | A61N 7/00 604/22 |
| 2012/0035464 | A1* | 2/2012 | Raju | A61N 7/02 600/411 |
| 2012/0046656 | A1* | 2/2012 | Brannan | A61B 18/06 606/28 |
| 2012/0209118 | A1* | 8/2012 | Warnking | A61B 8/085 600/439 |
| 2013/0041249 | A1* | 2/2013 | Salomir | A61N 7/02 600/411 |

FOREIGN PATENT DOCUMENTS

| | | | | |
|---|---|---|---|---|
| WO | WO 0243805 | A1* | 6/2002 | A61N 7/02 |
| WO | 2009124301 | A1 | 10/2009 | |
| WO | 2010082135 | A1 | 7/2010 | |
| WO | 2012052847 | A1 | 4/2012 | |

OTHER PUBLICATIONS

Foiret, "Spatial and Temporal Control of Hyperthermia Using Real Time Ultrasonic Thermal Strain Imaging with Motion Compensation, Phantom Study", 2015.*

Malinen, "Feedforward and feedback control of ultrasound surgery", Applied Numerical Mathematics 2006.*

Senneville et al., "Real-Time Adaptive Methods for Treatment of Mobile Organs by MRI-Controlled High-Intensity Focused Ultrasound", Magnetic Resonance in Medicins, 2007.*

Enholm J.K. et al "Improved Volumetric MR-HIFU Ablation by Robust Binary Feedback Control" IEEE Transactions on Biomedical Enginerring, vol. 57, No. 1 Jan. 1, 2010 p. 103-113.

Schlesinger et al "MR Guided Focused Ultrasound Surgery . . . " Medical Physics, vol. 40 No. 8, Jan. 1, 2013 p. 080901.

Ross et al, "Curvilinear Transurethral Ultrasound Applicator for Selective Prostate Thermal Therapy" Medical Physics, vol. 32 (6) Jun. 2005, p. 1555-1565.

Chopra et al "Method for MRI-Guided Conformal Thermal Therapy of Prostate with Planar Transurethral . . . " Physics Med. Biol. 50 (2005) p. 4957-4975.

Chopra et al, "MRI-Compatible Transurethral Ultrasound System for Treatment of Localized Prostate Cancer . . . " Medical Physics 35(4) Apr. 2008 p. 1346-1357.

\* cited by examiner

HIGH-INTENSITY FOCUSED ULTRASOUND IRRADIATION

CROSS-REFERENCE TO PRIOR APPLICATIONS

This application is the U.S. National Phase application under 35 U.S.C. § 371 of International Application No. PCT/IB2014/058890, filed on Feb. 11, 2014, which claims the benefit of U.S. Patent Application No. 61/768,774, filed on Feb. 25, 2013. These applications are hereby incorporated by reference herein.

FIELD OF THE INVENTION

The invention relates to the field of guided high-intensity focused ultrasound (HIFU) therapy.

BACKGROUND OF THE INVENTION

The invention pertains to guided high-intensity focused ultrasound (HIFU) therapy. An ultrasonic treatment device, i.e. a HIFU therapy module, directs the ultrasonic irradiation towards a target zone of a subject of interest, which is usually an alive being, more typically a human being.

Interstitial and intraluminal ultrasonic irradiation devices frequently comprise a mechanically movable transducer, which enables a movement of a beam path of the ultrasonic irradiation. An exemplary application is the treatment of prostate cancer with a rotatable intra-urethral transducer. Accordingly, the transducer is movable so as to control the position within a target zone where HIFU energy is deposited. An actuator is provided to move the transducer. The actuator is controlled by a control unit to move, i.e. to rotate, the transducer, so that a trajectory of HIFU energy depositions is generated. Accordingly, the entire target zone can be heated by the HIFU module as required for the treatment.

Diagnostic imaging like magnetic resonance imaging (MRI) is becoming more important in the area of therapy. In particular, diagnostic imaging is used to obtain temperature information of the target zone to monitor the heating of the target zone. This increases the accuracy of the treatment. Alternatively, also ultrasonic devices can be used as imaging devices in this area.

In current ultrasonic treatment systems comprising the diagnostic imaging device and the ultrasonic treatment device, the diagnostic imaging device is used for providing temperature information in the direction of the beam path of the ultrasonic irradiation. I.e. the diagnostic imaging device is configured to monitor the temperature in the area where the HIFU depositions, also referred to as sonications, are made. A control unit of the ultrasonic treatment device is configured to control the activation at the current target zone on the basis of the measured temperature. The heating is achieved by performing simultaneous sonication and displacement of the beam direction. This is for example proposed in the article "Method for MRI-guided conformal thermal therapy of prostate with planar transurethral ultrasound heating applicators" Rajiv Chopra, Mathieu Burtnyk, Masoom A Haider and Michael J Bronskill, Phys. Med. Biol. 50 (2005) 4957-4975. In particular, it is proposed to use the above interstitial and intraluminal ultrasonic irradiation unit, with an acoustic power and a rotation speed proportional to the difference between the targeted temperature and temperature measured along the sonication direction at the targeted location. This feedback temperature control deliver acoustic power until the target temperature is reached along the beam path at the current target location. However sonications along each direction overlap to some extent due to the width of the ultrasonic beam. Furthermore, the effect of thermal diffusion may result in a further heating of an area, when the ultrasonic beam does not cover this area anymore. As consequence for a specific beam path orientation, an additional temperature rise is taking place at this location once the beam is moved ahead. The heating in a location is completed only once the ultrasonic beam has moved sufficiently away from this location. As consequence the final temperature at the target contour overpass the targeted temperature by a value not predicted.

Accordingly, the control unit decides which sonication parameters such as acoustic power, ultrasound frequency and movement speed are to be applied based on the current temperature within the area of the current HIFU depositions. This requires an accurate calibration of the ultrasonic irradiation unit, in particular in respect to the direction of a beam path of the ultrasonic irradiation. Furthermore, due to beam parameters like beam width, some areas of the subject of interest can be exposed to a dose, which is higher than required. This extends the time required for the treatment of the subject of interest and can lead to undesired treatments of areas of the subject of interest outside the target zone.

SUMMARY OF THE INVENTION

It is an object of the invention to provide improvements for high-intensity focused ultrasonic irradiation heating, which overcome at least some of the above disadvantages. In particular, it is an object of the invention to provide an ultrasonic treatment device, an ultrasonic treatment system, and a method for ultrasonic treatment, which enable treatments based on high-intensity focused ultrasonic irradiation heating, which can be easily performed, which require few time for calibration purposes, which can be performed in a short time, which can be performed with high accuracy, and which comprise a low risk of damaging areas of a subject of interest outside a target area.

This object is achieved by an ultrasonic treatment device for heating a portion of a subject of interest, comprising an ultrasonic irradiation unit for generating high-intensity focused ultrasonic irradiation, whereby a beam path of the ultrasonic irradiation is movable along a trajectory for depositing ultrasonic energy within a target zone of the subject of interest, and a control unit for controlling the ultrasonic irradiation unit to move the beam path of the ultrasonic irradiation along the trajectory and to apply an ultrasonic dose to the target zone, wherein the control unit is adapted to receive temperature information of the target zone and to control the ultrasonic irradiation unit based on the received temperature information, and the control unit is adapted to control the ultrasonic irradiation unit based on the temperature of a current and at least one previous direction of the beam path of the ultrasonic irradiation along the trajectory.

This object is also achieved by an ultrasonic treatment system, comprising the above ultrasonic treatment device and a diagnostic imaging device for providing temperature information of a target zone of the subject of interest, wherein the control unit of the ultrasonic treatment device is adapted to receive the temperature information from the diagnostic imaging device.

This object is further achieved by a method for ultrasonic treatment for heating a portion of a subject of interest, comprising the steps of generating high-intensity focused ultrasonic irradiation, whereby a beam path of the ultrasonic irradiation is movable along a trajectory for depositing ultrasonic energy within a target zone of the subject of interest, controlling the ultrasonic irradiation to move the beam path of the ultrasonic irradiation along the trajectory and to apply an ultrasonic dose to the target zone, receiving temperature information of the target zone, and controlling the ultrasonic irradiation based on the received temperature information, wherein controlling of the ultrasonic irradiation is based on the temperature of a current and at least one previous direction of the beam path of the ultrasonic irradiation along the trajectory.

This object is also achieved by a software package for upgrading an ultrasonic treatment device, whereby the software package contains instructions for controlling the ultrasonic treatment device according to the above method.

This object is further achieved by a software package for upgrading an ultrasonic treatment system, whereby the software package contains instructions for controlling the ultrasonic treatment system according to the above method.

By looking at the temperature or a thermal dose distribution along a previous direction of the focus of the ultrasonic irradiation along the trajectory where the heating has been completed, an improved control of the treatment is achieved. Even if this previous sonication was different to the one currently applied, it has been found that this is a good indicator of the tissue and ultrasound system behavior. The control unit decides which ultrasonic dose is applied while the current heating along the moving focus of the ultrasonic irradiation trajectory is not finalized. The ultrasonic dose refers to sonication parameters such as acoustic power, ultrasound frequency and rotation speed.

The control of the ultrasonic dose can be based on the temperature as provided by the diagnostic imaging device or on the calculation of a thermal dose based on the temperature as provided by the diagnostic imaging device. Both approaches have proven reliable. The thermal dose defined in Equivalent Minutes to a heating at 43° C. (EM) refers to an evaluation of a time and temperature sufficient to obtain a desired impact on a tissue of the target zone. Typical thermal dose threshold to assess tissue ablation is 240 EM. Different methods can be used to determine the temperature or thermal dose reached along the trajectory of the beam path of the ultrasonic irradiation for a previous position of the beam path, in which the sonication has already been completed.

A simple temperature driven approach comprises the use the maximum temperature detected located backward, i.e. along the previous directions of the ultrasonic irradiation along the trajectory. This method is relatively easy to implement because there is no need to estimate precisely how much backward in terms of time or position a sonication has been completed. This method independent of the movement speed, and the target contour is relatively robust. According to a preferred embodiment, the search of the maximum temperature is restricted to a relevant range of positions and/or temporal positions of the beam path of the ultrasonic irradiation. Most preferably, the search of the maximum temperature is restricted to a predefined static range. For devices with a rotating beam path of the ultrasonic irradiation, the positions refer to angular positions. For such devices, preferred predefined ranges can be e.g. [−10°; 0° ] or [−60 s; 0 s], where 0° or 0 s represent the current position of the beam path. In an alternative embodiment, a dynamic range of temperature values is processed, whereby the range is adjusted as function of the movement speed. Narrowing the number of individual measurement points, i.e. voxels in the case of a magnetic resonance imaging device, allows to reduce the system sensitivity to imaging artifacts and to improve the system robustness.

Once the maximal temperature $T_{max}$ along the trajectory is detected, this value can be used to perform any type of feedback control. Preferably, a simple binary temperature regulation algorithm based on $T_{max}$ is used. Such an algorithm has achieved very accurate temperature control along the trajectory. Further preferred, this algorithm uses a minimal movement speed, e.g. a rotation rate, when $T_{max}$ is lower than the target temperature and uses a maximal movement speed in the opposite case. Further preferred, this algorithm uses a maximal sonication power when $T_{max}$ is lower than the target temperature and uses a minimal sonication power in the opposite case.

The invention enables thermotherapy based on ultrasonic irradiation, where the diagnostic imaging device is used for the guidance of the thermotherapy. The diagnostic imaging device can be used from treatment planning up to control of the spatial heating pattern in the subject of interest during the treatment. Preferably, the diagnostic imaging device is used for data flow for real-time analysis. Together with multiple sonication parameters, which can be controlled, including ultrasonic energy, frequency, and beam path direction/movement, a powerful ultrasonic treatment system is provided. The control based on the temperature of a current and at least one previous direction of the beam path of the ultrasonic irradiation along the trajectory enables improved temperature control. Enhanced spatial and temporal accuracy of the diagnostic imaging system improves the robustness to system imperfections and tissue heterogeneities. Preferably, the control unit comprises a binary controller based on fuzzy logic to regulate the temperature.

Advantages of the control based on the temperature of a current and at least one previous direction of the ultrasonic irradiation along the trajectory are, that the control is not dependent on tissue parameters and that no fine power calibration or tuning of gain parameters are necessary. The system is robust to misalignments of the beam path of the ultrasonic irradiation, since control is based on measured temperatures, which are not only acquired at the intended direction of the beam path.

Further advantages of the control based on the temperature of a current and at least one previous direction of the ultrasonic irradiation along the trajectory are a high temperature accuracy of about 1° C., low controller response time of one dynamic duration+60 ms, and a spatial resolution of the heating control of about 1 mm. In applications for prostate treatment, a volume ranging from 1 to 3 cm radius can be ablated in 40 minutes.

The target zone refers to the area of the subject of interest containing the tissue which has to be heated according to pre-defined parameters of the treatment. The trajectory is defined based on the target zone, where the ultrasonic energy is to be deposited, and can be a circular trajectory or a linear trajectory depending on the type of ultrasonic treatment device and the desired treatment.

The beam path of the ultrasonic irradiation usually has a certain width and includes areas affected to ultrasonic irradiation. The beam path has a direction, which refers to a main direction of the ultrasonic irradiation, e.g. the direction to which the highest ultrasonic power is irradiated.

It is to be noted that receiving temperature information of the target zone includes receiving temperature information from outside the target zone, which can be processed to derive temperature information of the target zone. The treatment typically requires the control of the temperature within the target zone, which is difficult to derive since different tissue parameters make the interpolation of temperatures difficult. Nevertheless, in case the tissue parameters are known, the knowledge of the temperature outside the target zone can enable a sufficiently reliable interpolation of the temperature of a certain point of the target zone, e.g. a contour of the target zone.

The ultrasonic treatment device can be used individually or together with another treatment device. The other treatment device can be e.g. a linear accelerator device (linac) or chemotherapy treatment device. These treatment devices can support the ultrasonic treatment depending on the requirements.

In the ultrasonic treatment system, the diagnostic imaging device and the ultrasonic treatment device are preferably connected via an electric or electronic interface, so that the temperature information can be directly passed from the diagnostic imaging device to the ultrasonic treatment device. Preferably, information is also passed from the ultrasonic treatment device to the diagnostic imaging device. This information may comprise information regarding the target zone, so that the ultrasonic treatment device can acquire the temperature information in particular in the target zone.

According to a preferred embodiment the ultrasonic irradiation unit comprises an ultrasonic transducer for generating the ultrasonic irradiation and an actuator for moving the beam path of the ultrasonic irradiation. The ultrasonic irradiation unit moves the beam path of the ultrasonic irradiation by a mechanical movement of the transducer. Different kinds of movement of the transducer can be implemented, as described in detail below. Control of the movement of the transducer can easily be implemented using the actuator. The transducer can comprise an array of transducer elements, which are commonly arranged and controlled by the control unit. For example, an intra-urethral transducer may comprise multiple transducer elements, which are arranged in a line, i.e. an array with a width of one element. This enables e.g. the treatment of the entire prostate of the subject of interest with one session, since the length of the transducer is sufficient to cover the entire prostate in this direction.

According to a preferred embodiment the ultrasonic transducer is a rotatable transducer and the actuator is a rotating actuator. Accordingly, the transducer is suitable to cover the entire surrounding around its rotational axis. Such an ultrasonic irradiation unit can be provided with small dimensions. E.g. interstitial and intraluminal ultrasound devices are frequently associated to a mechanically rotatable system to extend the coverage of the performed treatment.

According to a preferred embodiment the ultrasonic transducer is an axially movable transducer and the actuator is a lineal actuator. The transducer can be movable along one axis, or within a plane, i.e. along two axes. The transducer may have one lineal actuator for each axis or one actuator for a planar movement.

According to a preferred embodiment the ultrasonic irradiation unit comprises an ultrasonic transducer with an array of transducer elements, and the beam path of the ultrasonic irradiation is movable by electronically steering the relative phases of the transducer elements. This transducer does not necessarily require mechanically movable parts, it allows rapid adjustment of the location of the beam path of the ultrasonic irradiation.

According to a preferred embodiment the ultrasonic irradiation unit comprises multiple ultrasonic transducers, and the control unit is adapted to control the multiple ultrasonic transducers individually based on the temperature of a current and at least one previous direction of the beam path of the ultrasonic irradiation along the trajectory of each transducer. The multiple ultrasonic transducers enable an improved heating of the target zone. A homogenous heating can be achieved, since the multiple transducers focus the ultrasonic energy on multiple areas of the target zone at the same time, Nevertheless, individual control enables a reliable control of the treatment for the entire target zone. With the use of multiple ultrasonic transducers, the heating can be achieved in a reduced time. Each transducer may be provided with an array of individual transducer elements.

According to a preferred embodiment the ultrasonic irradiation unit comprises multiple actuators, and the control unit is adapted to control the multiple actuators individually based on the temperature of a current and at least one previous direction of the beam path of the ultrasonic irradiation along the trajectory of each transducer. Accordingly, the ultrasonic irradiation unit can be provided having multiple channels, which are controlled individually. A backward feedback can be implemented by considering the direction of the beam path of the ultrasonic irradiation and the trajectory for each channel. In an alternative embodiment, the actuators are commonly controlled, or one actuator is provided for moving the multiple transducers.

According to a preferred embodiment the control unit is adapted to receive temperature information of a contour of the target zone, and the control unit is adapted to control the ultrasonic irradiation unit based on temperatures at the contour of the target zone corresponding with the current and at least one previous direction of the ultrasonic irradiation. In the corresponding method the step of controlling the ultrasonic irradiation based on the received temperature information comprises controlling the ultrasonic irradiation based on the temperature of a target contour at a current and at least one previous direction of the beam path of the ultrasonic irradiation. With the temperature of the contour of the target zone, only few temperature values have to be provided along the trajectory of the movement of the beam path of the ultrasonic irradiation, so that processing of the data is facilitated. Furthermore, from the contour of the target zone, the temperature of a current and at least one previous direction of the ultrasonic irradiation along the trajectory can be easily selected. For example in the case of a control based on the maximum temperature of a previous direction of the ultrasonic irradiation, this temperature can be easily detected within the provided temperature values of the contour of the target zone. Since the contour defines the limit of the treatment, damages of tissues outside the target zone can be avoided.

According to a preferred embodiment the control unit is adapted to control the ultrasonic irradiation unit based on the temperature of a current and multiple previous directions of the beam path of the ultrasonic irradiation along the trajectory. The temperatures of several backward orientations of the beam path of the ultrasonic irradiation are considered to evaluate the one which indicates the largest controlled values along the beam path in terms of average or peak values.

According to a preferred embodiment the diagnostic imaging device is a magnetic resonance imaging device or an ultrasonic imaging device. Both devices can be operated during the treatment, preferably in real-time, so that feedback control of the sonication can be applied. Preferably, the diagnostic imaging device provides a 3-dimensional diagnostic image. In particular, in the case of an ultrasonic irradiation unit having a rotatable transducer, also one or multiple 2-dimensional diagnostic images can be used, whereby the rotational axis has a rectangular angle in respect to the two dimensions of the image.

BRIEF DESCRIPTION OF THE DRAWINGS

These and other aspects of the invention will be apparent from and elucidated with reference to the embodiments described hereinafter. Such an embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
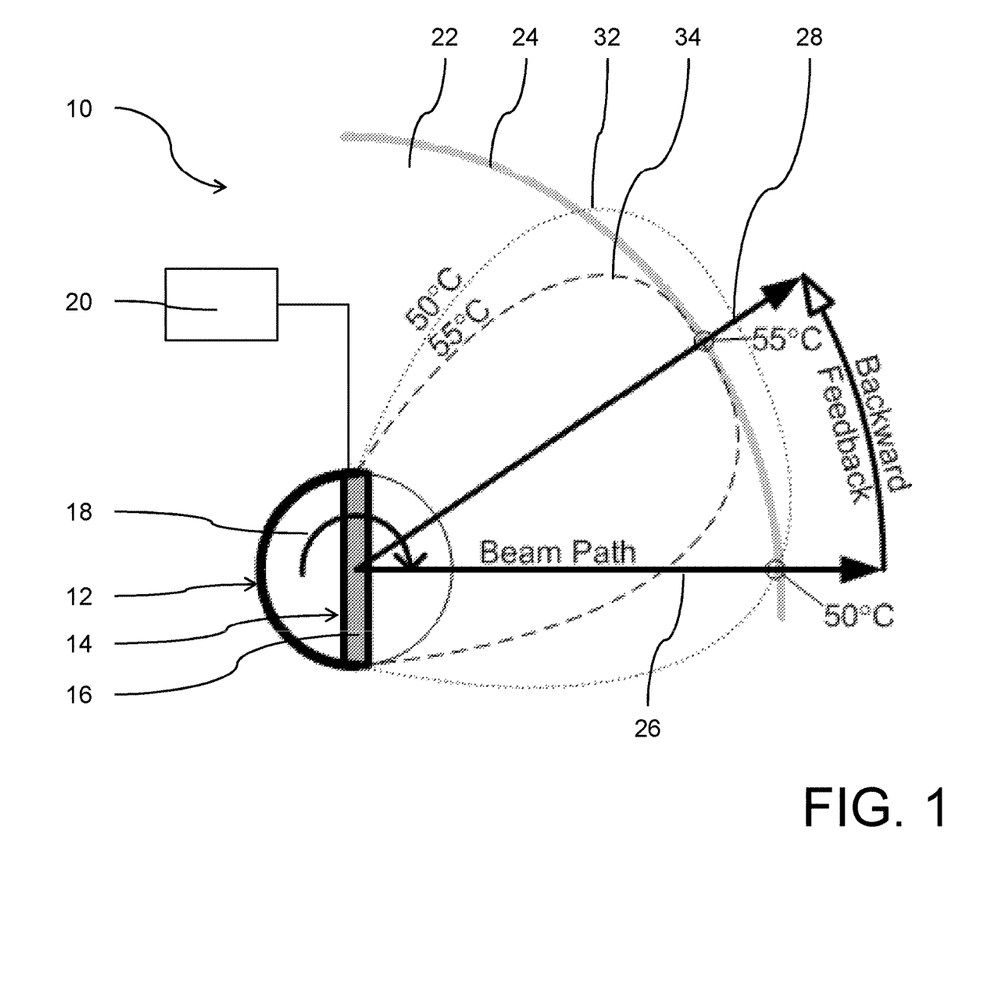
FIG. 1 is a schematic figure indicating the behavior of an ultrasonic treatment device according to a preferred embodiment.
Figure 2:
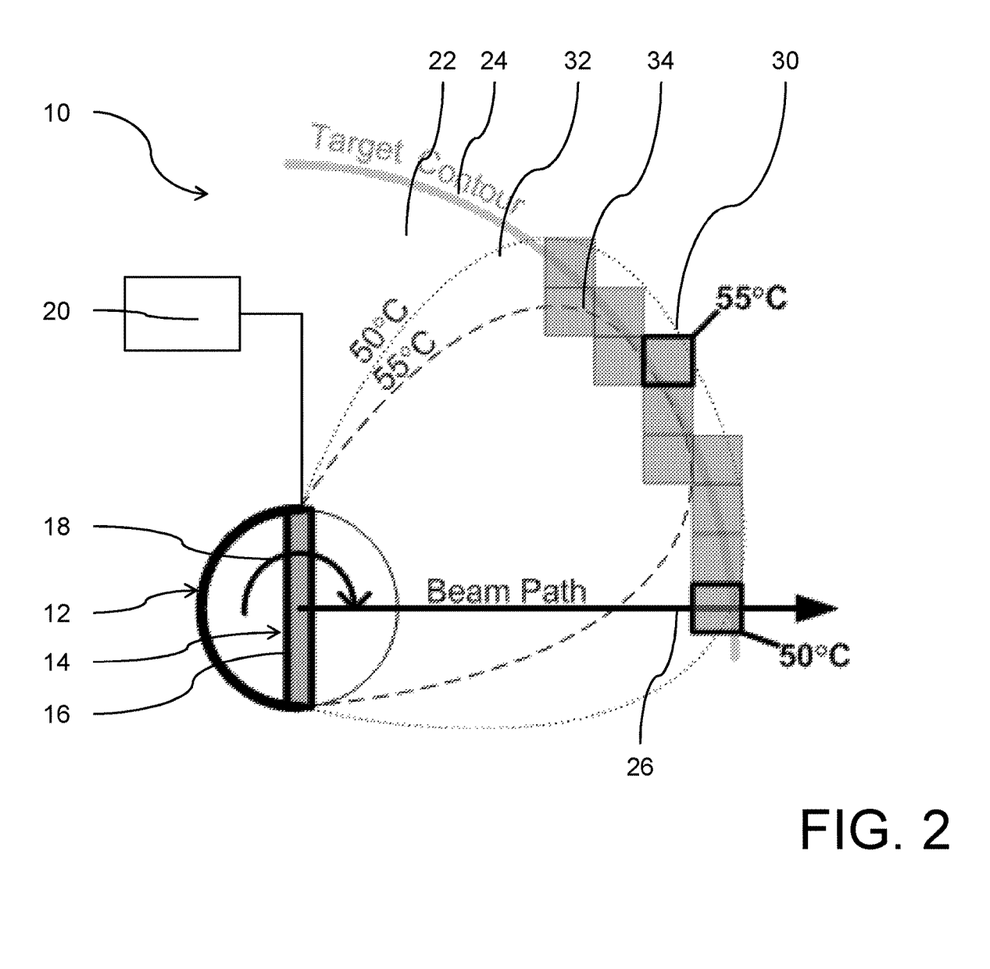
FIG. 2 is a schematic figure indicating the behavior of an ultrasonic treatment device according to a preferred embodiment according to FIG. 1 with additionally shown voxels representing temperature measurement values.

FIGS. 1 and 2 show an ultrasonic treatment device 10 according to a preferred embodiment. The ultrasonic treatment device 10 in this embodiment is an intra-urethral device a used for thermal treatments of the prostate.

The ultrasonic treatment device 10 comprises an ultrasonic irradiation unit 12 for generating high-intensity focused ultrasonic irradiation, also referred to as HIFU. The ultrasonic irradiation unit 12 comprises an ultrasonic transducer 14 for generating a beam path of ultrasonic irradiation, whereby the transducer 14 comprises an array of transducer elements 16, from which only one transducer element 16 is visible in FIGS. 1 and 2. The transducer elements 16 are arranged in a line along the longitudinal axis of the transducer 14. The ultrasonic transducer 14 is rotatable along its longitudinal axis.

The beam path of the ultrasonic irradiation has a width and includes areas affected to ultrasonic irradiation. The beam path has a direction, which refers to a main direction of the ultrasonic irradiation, e.g. the direction to which the highest ultrasonic power is irradiated.

The ultrasonic irradiation unit 12 further comprises an actuator for moving the beam path of the ultrasonic irradiation, which is schematically indicated by arrow 18. The actuator 18 in this embodiment is a rotating actuator for rotating the transducer 14 entirely along its rotational axis. Together with the transducer 14, the beam path of the ultrasonic irradiation is movable along a trajectory for depositing ultrasonic energy within a target zone 22 of a subject of interest. The target zone 22 refers to the area of the subject of interest containing the tissue to be heated according to pre-defined parameters of a treatment.

The ultrasonic treatment device 10 comprises a control unit 20 for controlling the ultrasonic irradiation unit 12 to move the beam path of the ultrasonic irradiation by controlling the actuator 18 and the transducer 14. In particular, the control unit 20 controls the rotational speed of the actuator 18 and sonication parameters of the transducer 14, which include energy and frequency of the ultrasonic irradiation.

An ultrasonic treatment system, which is in its entirety not shown in the figures, comprising the above ultrasonic treatment device 12 and a diagnostic imaging device for providing temperature information of the target zone 22 of a subject of interest. The diagnostic imaging device in this embodiment is a magnetic resonance imaging (MRI) device capable of real-time operation to provide feedback to the control unit 20 of the ultrasonic treatment device 10.

The diagnostic imaging device and the ultrasonic treatment device 10 are connected via an electronic interface, so that the temperature information can be directly passed from the diagnostic imaging device to the control unit 20. The temperature information in this embodiment refers to the temperature of a contour 24 of the target zone 22 covering a current 26 and previous directions 28 of the beam path of the ultrasonic irradiation, as indicated with one previous direction 28 in FIG. 1. The control unit 20 is adapted to receive this temperature information via the electronic interface.

The control unit 20 is adapted to control the ultrasonic irradiation unit 12 based on the received temperatures at the contour 24 of the target zone 22 corresponding with the current and a previous direction 26, 28 of the beam path of the ultrasonic irradiation. In the preferred embodiment, control of the ultrasonic irradiation unit 12 via the control unit 20 is based on the maximum temperature of the contour 24, where the beam path of the ultrasonic irradiation has already passed by. As indicated in FIG. 2, this temperature is detected within the provided temperature values of the contour 24 of the target zone 22. The temperature values correspond to voxels 30 of the MRI device.

In this embodiment, the control unit 20 performs a control by looking at the temperature along previous directions 28 of the beam path of the ultrasonic irradiation, i.e. along trajectory corresponding to the contour 24, where the heating has been completed. The control unit 24 decides which ultrasonic dose is applied while the current heating along the moving beam path of the ultrasonic irradiation trajectory is not finalized, and controls the ultrasonic irradiation unit 12 accordingly. The ultrasonic dose refers to sonication parameters such as acoustic power, ultrasound frequency and rotation speed.

The control of the ultrasonic dose is based on the temperature as provided by the MRI device. In this embodiment, a temperature driven approach is used. This comprises the use the maximum temperature detected among the temperature values of the contour 24 of the previous directions 28 of the ultrasonic irradiation along the trajectory. Once the maximal temperature $T_{max}$ along the trajectory is detected, this value is used to perform feedback control with a binary temperature regulation algorithm. This algorithm uses a minimal rotation rate, when $T_{max}$ is lower than a target temperature, and uses a maximum movement speed in the opposite case. This algorithm is implemented in the control unit 20 with a binary controller based on fuzzy logic.

While the ultrasonic dose is applied to the target zone 22 upon control of the control unit 20, a portion of a subject of interest is heated. In particular, the target zone 22 is heated to apply an ultrasonic dose to achieve the heating of the target zone 22. The effect of the application of the ultrasonic dose can be seen in FIGS. 1 and 2 by lines 32, 34, which correspond to isotherms of 50° C. and 55° C., respectively. When applying the ultrasonic dose, the transducer 14 of the ultrasonic irradiation unit 12 is rotated, so that the beam path of the ultrasonic irradiation is moved along the contour 24 of the target zone 22. This movement corresponds to the trajectory, where the ultrasonic energy is to be deposited, and is a circular trajectory in this embodiment.

Figure 3:
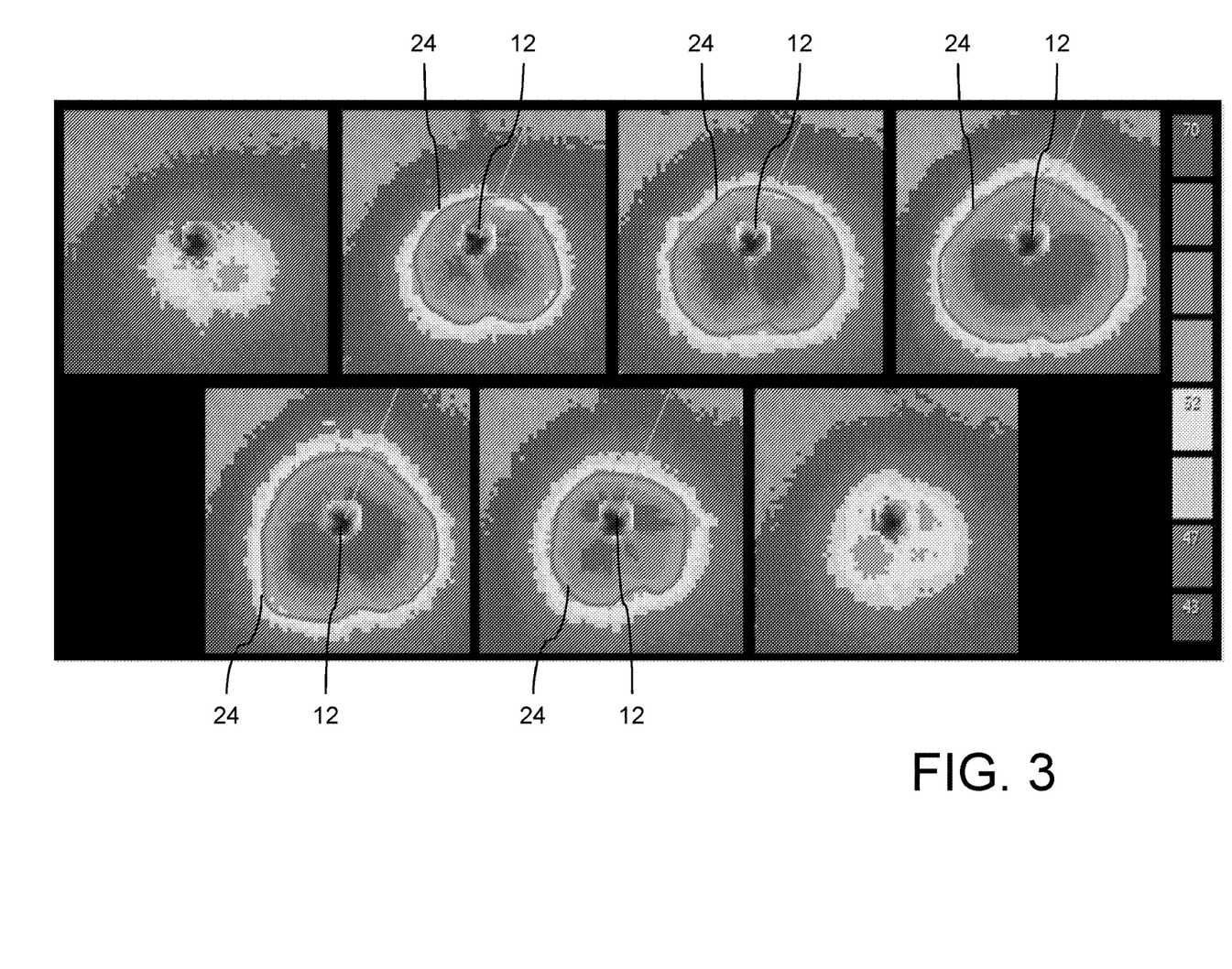
FIG. 3 shows a set of thermal maps showing the maximum temperature distribution at the end of sonication.

FIG. 3 shows a set of thermal maps showing the benefits of the temperature control of the preferred embodiment. As can be seen in the thermal maps, a homogonous maximum temperature distribution is achieved at the end of sonication along the rotational axis of the ultrasonic irradiation unit 12. In the five central slices aligned with the five transducer elements 16 of the ultrasonic irradiation unit 12, the 52° C.

transition line between the red and yellow colored voxels 30 matches the location of the initially planned prostate target contour 24 with an average accuracy of one voxel 30. The first and last slices provide a safety margin such that no excessive heating diffuses outside of the target zone 22.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST 10 ultrasonic treatment device
12 ultrasonic irradiation unit
14 ultrasonic transducer
16 transducer element
18 actuator, arrow
20 control unit
22 target zone
24 contour
26 current direction
28 previous direction
30 voxel
32 line, 50° C. isotherm
34 line, 55° C. isotherm

The invention claimed is:

1. An ultrasonic treatment device comprising:
an ultrasonic irradiation unit arranged to generate an ultrasonic irradiation, wherein a beam path of the ultrasonic irradiation is movable along a trajectory for depositing ultrasonic energy within a target zone within a portion of a subject, and
a controller programmed to:
control the ultrasonic irradiation unit to control movement of the beam path of the ultrasonic irradiation along the trajectory and to apply an ultrasonic dose to the target zone,
receive temperature information of the target zone, and
control the ultrasonic irradiation unit to perform temperature-driven feedback control of the ultrasonic dose to the target zone using the temperature of a current beam path and a maximum temperature of at least one previous direction of the beam path of the ultrasonic irradiation along the trajectory wherein the temperature-driven feedback control of the ultrasonic dose to the target zone includes using a minimal movement speed when the maximum temperature is lower than a target temperature and using a maximum movement speed when the maximum temperature is not lower than the target temperature.

2. The ultrasonic treatment device according to claim 1, wherein the ultrasonic irradiation unit comprises an ultrasonic transducer for generating the ultrasonic irradiation and an actuator for moving the beam path of the ultrasonic irradiation.

3. The ultrasonic treatment device according to claim 2, wherein the ultrasonic transducer is a rotatable transducer and the actuator is a rotating actuator and the temperature-driven feedback control of the ultrasonic dose to the target zone includes using a minimum rotation rate for the rotatable transducer when the maximum temperature is lower than a target temperature and using a maximum rotation rate for the rotatable transducer when the maximum temperature is not lower than the target temperature.

4. The ultrasonic treatment device according to claim 2, wherein the ultrasonic transducer is an axially movable transducer and the actuator is a lineal actuator.

5. The ultrasonic treatment device according to claim 1, wherein the ultrasonic irradiation unit comprises an ultrasonic transducer,
wherein the ultrasonic transducer comprises an array of transducer elements,
wherein the beam path of the ultrasonic irradiation is movable by electronically steering the relative phases of the transducer elements.

6. The ultrasonic treatment device according to claim 1, wherein the ultrasonic irradiation unit comprises multiple ultrasonic transducers,
wherein the controller is programmed to control the multiple ultrasonic transducers individually based on the temperature of a current beam path and of at least one previous direction of the beam path of the ultrasonic irradiation along the trajectory of each transducer.

7. The ultrasonic treatment device according to claim 2, wherein the ultrasonic irradiation unit comprises multiple ultrasonic transducers, and
wherein the controller is programmed arranged to control the multiple ultrasonic transducers individually based on the temperature of a current beam path and of at least one previous direction of the beam path of the ultrasonic irradiation along the trajectory of each transducer.

8. The ultrasonic treatment device according to claim 1, wherein the controller is programmed to:
receive temperature information of a contour of the target zone, and
control the ultrasonic irradiation unit based on temperatures at the contour of the target zone corresponding with the current beam path and of at least one previous direction of the beam path of the ultrasonic irradiation.

9. An ultrasonic treatment system, comprising:
the ultrasonic treatment device according to claim 1, and
a diagnostic imaging device arranged to provide temperature information of a target zone,
wherein the controller of the ultrasonic treatment device is programmed to receive the temperature information from the diagnostic imaging device.

10. The ultrasonic treatment device according to claim 9, wherein the diagnostic imaging device is one of a magnetic resonance imaging device or an ultrasonic imaging device.

11. A method for ultrasonic heating of a portion of a subject, the method comprising:
generating high-intensity focused ultrasonic irradiation, whereby a beam path of the ultrasonic irradiation is movable along a trajectory for depositing ultrasonic energy within a target zone of the subject,
moving the beam path of the ultrasonic irradiation along the trajectory,
applying an ultrasonic dose to the target zone,
receiving temperature information of the target zone, and
controlling the ultrasonic irradiation based on the received temperature information, wherein controlling of the ultrasonic irradiation is performed using the temperature of a current beam path and of at least one previous direction of the beam path of the ultrasonic irradiation along the trajectory, and wherein controlling of the ultrasonic dose to the target zone includes using a minimal movement speed when a maximum temperature is lower than a target temperature and using a maximum movement speed when the maximum temperature is not lower than the target temperature.

12. The method according to claim 11, wherein the controlling the ultrasonic irradiation based on the received temperature information comprises controlling the ultrasonic irradiation based on the temperature of a target contour at a current beam path and of at least one previous direction of the beam path of the ultrasonic irradiation.

13. A non-transitory computer readable medium storing instructions for controlling the ultrasonic treatment device according to the method of claim 11.

14. The ultrasonic treatment device according to claim 7, wherein the ultrasonic irradiation unit comprises multiple actuators,
wherein the controller is programmed to control the multiple actuators individually based on the temperature of a current beam path and of at least one previous direction of the beam path of the ultrasonic irradiation along the trajectory of each transducer.

15. The method according to claim 11, wherein the controlling the ultrasonic irradiation based on the received temperature information comprises:
controlling the ultrasound irradiation using a maximum temperature detected along the previous directions of the beam path of the ultrasonic irradiation along the trajectory.

16. The ultrasonic treatment device according to claim 1 wherein the controller is further programmed to restrict a search of the maximum temperature to a predefined static temperature range; and
the ultrasonic irradiation unit is configured to generate a rotating beam path of ultrasonic irradiation angular positions.

17. The ultrasonic treatment device according to claim 1, wherein the controller is further programmed to:
restrict a search of the maximum temperature to a dynamic temperature range by adjusting the temperature range as a function of a movement speed of the beam path of the ultrasonic irradiation.

18. The ultrasonic treatment device according to claim 1, wherein the controller is further programmed to:
perform feedback control using the maximum temperature along the trajectory.

19. An ultrasonic treatment device comprising:
at least one ultrasonic transducer configured to generate an ultrasonic irradiation;
at least one actuator configured to move a beam path of the generate ultrasonic irradiation along a trajectory for depositing ultrasonic energy within a target zone within a portion of a subject, and
a controller programmed to:
control the ultrasonic irradiation unit movement of the beam path of the ultrasonic irradiation along the trajectory and to apply an ultrasonic dose to the target zone,
receive temperature information of the target zone and to control the ultrasonic irradiation unit based on the received temperature information, and
control the ultrasonic irradiation unit using the temperature of a current beam path and of a maximum temperature of at least one previous direction of the beam path of the ultrasonic irradiation along the trajectory wherein the control of the ultrasonic dose to the target zone includes using a minimal movement speed when the maximum temperature is lower than a target temperature and using a maximum movement speed when the maximum temperature is not lower than the target temperature.

* * * * *